United States Patent [19]

Emery et al.

[11] Patent Number: 5,202,252
[45] Date of Patent: Apr. 13, 1993

[54] MONOCLONAL ANTIBODIES AGAINST LENS EPITHELIAL CELLS AND METHODS FOR PREVENTING PROLIFERATION OF REMNANT LENS EPITHELIAL CELLS AFTER EXTRACAPSULAR EXTRACTION

[75] Inventors: Jared M. Emery, Houston; Dominic M-K Lam; Peter J. Kelleher, both of The Woodlands, all of Tex.

[73] Assignee: Houston Biotechnology Inc., The Woodlands, Tex.

[21] Appl. No.: 206,610

[22] Filed: Jun. 14, 1988

Related U.S. Application Data

[60] Continuation-in-part of Ser. No. 905,735, Sep. 9, 1986, abandoned, which is a continuation of Ser. No. 472,795, Mar. 7, 1983, abandoned, which is a division of Ser. No. 355,081, Mar. 5, 1982, Pat. No. 4,432,751.

[51] Int. Cl.$^5$ ............... C12N 5/12; C07K 15/28
[52] U.S. Cl. ............... 435/240.27; 530/388.2; 530/391.3; 530/391.1
[58] Field of Search ............... 435/240.27, 70.21, 172.2; 935/104, 107, 110; 424/85.8; 530/387, 388.2, 391.1, 391.3

[56] References Cited

U.S. PATENT DOCUMENTS

| | | | |
|---|---|---|---|
| 4,340,535 | 7/1982 | Voisin et al. | 260/112 B |
| 4,432,751 | 2/1984 | Emery et al. | 604/49 |
| 4,590,071 | 5/1986 | Scannon et al. | 424/85 |
| 4,698,420 | 10/1987 | Urnovitz | 530/387 |

FOREIGN PATENT DOCUMENTS

| | | |
|---|---|---|
| 44167 | 1/1982 | European Pat. Off. |
| 173648 | 5/1986 | European Pat. Off. |
| 140109 | 8/1986 | European Pat. Off. |
| WO88/02594 | 4/1988 | PCT Int'l Appl. |
| WO89/08474 | 9/1989 | PCT Int'l Appl. |

OTHER PUBLICATIONS

Samuel Fulcher, et al. "Use of Immunotoxin to Inhibit Proliferating Human Corneal Endothelium," *Investigative Opthalmology & Visual Science*, vol. 29, May, 1988, pp. 755–759.

Thomas J. Hansen, et al., "Methotrexate–Anticollagen Conjugate Inhibits In Vitro Lens Cell Outgrowth," *Investigative Opthalmology & Visual Science*, vol. 28, Jul., 1987, pp. 1206–1209.

Zam, Z. S., et al, Cancer Eye Research, 1(3):139–144 (1981).

Carper, D. et al., Developmental Biology, 113:104–109 (1986).

*Primary Examiner*—David L. Lacey
*Assistant Examiner*—Susan L. Futrovsky
*Attorney, Agent, or Firm*—Barbara Rae-Venter

[57] ABSTRACT

Compositions and methods for their use are provided for preventing proliferation of remnant lens epithelial cells following extracapsular extraction. Complement-fixing monoclonal antibodies specific for lens epithelial cells are introduced into the anterior chamber of the eye. Following binding of the monoclonal antibody to any lens epithelial cells, complement is introduced into the anterior chamber effecting lysis of the remnant lens epithelial cells. The method may be used at the time of extracapsular cataract extraction or may be used subsequently to remove a second cataract resulting from proliferation of remnant lens epithelial cells.

17 Claims, No Drawings

MONOCLONAL ANTIBODIES AGAINST LENS EPITHELIAL CELLS AND METHODS FOR PREVENTING PROLIFERATION OF REMNANT LENS EPITHELIAL CELLS AFTER EXTRACAPSULAR EXTRACTION

CROSS-REFERENCE TO RELATED APPLICATIONS

This application is a continuation-in-part of application Ser. No. 905,735, filed Sep. 9, 1986, now abandoned which is a continuation of application Ser. No. 472,795, filed Mar. 7, 1983, now abandoned, which is a divisional of application Ser. No. 355,081, filed Mar. 5, 1982, now U.S. Pat. No. 4,432,751, issued Feb. 21, 1984, which disclosures are incorporated herein by reference.

INTRODUCTION

1. Technical Field

The field concerns methods and compositions for inhibiting proliferation of remnant lens epithelial cells.

2. Background

Extracapsular cataract extraction is a desirable method for removing cataracts. With this technique there is a lower incidence of post-operative complications such as cystoid macular edema and retinal detachment. The availability of an improved extracapsular extraction technique such as phacoemulsification and the requirement for an intact posterior lens capsule for implantation of a wide variety of intraocular lenses has further supported use of extracapsular cataract extraction for removing cataracts.

Extracapsular lens extraction is accompanied by a significant incidence of posterior lens capsule opacification, which may require additional surgical procedures such as posterior capsulotomy or repolishing of the posterior lens capsule in order to obtain good vision. The pathogenesis of posterior lens capsule opacification after extracapsular cataract extraction is due to proliferation of remnant lens epithelial cells on the posterior lens capsule to form abortive lens "fibers" and "bladder" cells ("Elschnig's pearls").

To inhibit secondary cataract formation, a variety of techniques have been used. Roy et al., *Contact and Intraocular Lens Medical Journal* (1979) 5:175-178 reported the use of vincristine and vinblastine as a means of inhibiting lens cell proliferation. Radiation treatment has also been tried, and reported to be promising. Instillation of methotrexate and retinoic acid into the anterior chamber of the eye has also been tried to prevent posterior lens capsule opacification. However these treatment regimens lack specificity; they do not distinguish between lens epithelial cells and other cell types present in the anterior chamber and as a result of these treatments other (desirable) cells may be damaged. It is therefore of interest to develop methods and compositions which would provide for selective destruction of remnant lens epithelial cells as a means of preventing formation of secondary cataracts and posterior lens capsule opacification.

RELEVANT LITERATURE

Production of monoclonal antibodies has been described. See, for example, *Monoclonal Antibodies*, eds. Roger H. Kennett, Thomas J. McKearn, Kathleen B. Bechtol, Plenum Press, New York, 1980; *Nature* (1975) 256:495-497; U.S. Pat. Nos. 4,271,145; 4,196,265; 4,172,124; 4,195,125; 4,262,090; and 4,294,927.

SUMMARY OF THE INVENTION

Methods and compositions are provided for inhibiting posterior lens capsule opacification following extracapsular cataract extraction. The methods involve introducing complement fixing monoclonal antibodies substantially specific for lens epithelial cells into the anterior chamber of the eye concurrently with or subsequent to extracapsular cataract extraction. Complement is then introduced into the anterior chamber, effecting selective lysis of the lens epithelial cells.

DESCRIPTION OF THE SPECIFIC EMBODIMENTS

Methods and compositions are provided for inhibiting proliferation of remnant lens epithelial cells after extracapsular extraction. The method comprises introducing into the anterior chamber of the eye, at the time of original cataract removal or subsequently, complement-fixing monoclonal antibodies specific for lens epithelial cells which bind to any remnant lens epithelial cells. The antibodies are substantially specific for lens epithelial cells and have low or no cross-reactivity with other cells found in the anterior chamber. Following a sufficient time for the antibody to bind to any remnant lens epithelial cells, complement is introduced into the anterior chamber, effecting selective lysis of the lens epithelial cells.

The monoclonal antibody is capable of binding substantially specifically to lens epithelial cells, as compared to other cells which may be present in or in contact with the anterior chamber of the eye, such as fibroblasts, melanocytes, corneal endothelial cells, etc., desirably also other epithelial cells, e.g., corneal epithelial cells. The monoclonal antibody may be produced as a result of hybridoma formation and expression by the hybridoma, whether in culture or present as ascites. The monoclonal antibodies may be derived either from a single hybridoma cell line or may be a mixture or "cocktail" of two or more monoclonal antibodies derived from different hybridoma cell lines, where the antibodies would bind to different antigenic moieties on lens epithelial cells.

The monoclonal antibodies may be any mammalian species, including murine, rabbit, human or the like, or combinations thereof, such as chimeric antibodies, having for example a human $CH_2$ domain or the Fc portion of the molecule, and a mouse or other mammalian source variable region. The antibodies may be any class or subclass which will activate complement, such as IgM, IgG, 2a, 2b, or 3 or the human equivalent thereof (for a description of complement-fixing classes and subclasses, see *Monoclonal Antibodies: Principles and Practice*, 2nd ed., Goding, Academic Press, New York, pg. 14, 1986, which publication is incorporated herein by reference).

The methods for preparing monoclonal antibodies are well established. They may be prepared by any methods known to those skilled in the art. Various lens epithelial cells may be used as the immunogen, particularly human lens epithelial cells, although other species may find use, e.g., primates. Whole cells are preferred, however homogenates, membrane fragments or the like, can be used. The source of the cells includes cells growing in tissue culture, or tissues removed during cataract surgery. Thus, human lens epithelial cells from tissues removed during cataract surgery or within a short time after death, preferably within approximately 30 minutes after death may be used directly, or the cells may be maintained by placing the surgical specimens in tissue culture using well established techniques.

In accordance with the subject invention, a mammal, conveniently a mouse or other small mammal, is hyperimmunized with the immunogen. Methods of immunization are well known and are amply described in the literature. The immunogenic material, generally about $10^5$ to about $10^6$ cells or cell equivalents, is injected with or without adjuvant into the mammal, or by repeated injections over relatively short periods of time. To ensure the hyperimmunization of the animal, 2-6 subsequent booster injections are administered. The animals are then killed, usually within 1-5 days after the last injection. The spleen is removed, and the spleen cells immortalized, usually by fusion with an appropriate myeloma cell line.

The method of cell fusion is not a critical portion of this invention and various techniques may be employed. Generally a nonionic detergent, for example polyethylene glycol (PEG), is used as the fusogen. The spleen cells and the myeloma cells are combined in the presence of the nonionic detergent, conveniently PEG 1540 and other additives, for example, serum-free Dulbecco's Modified Eagle's Medium (SF-DMEM), for approximately 5 minutes. The excess nonionic detergent is then rapidly removed by washing the cells.

The cells are promptly dispensed into small culture wells at a relatively low density, ranging from about $1 \times 10^5$/well to about $5 \times 10^5$/well in appropriate medium, commonly a selective medium comprising hypoxanthine, aminopterin and thymidine (HAT) medium.

After a sufficient period, usually one to two weeks, colonies of hybrids are observed. The colonies are then screened for antibodies which bind specifically to lens epithelial cells. The colonies are additionally screened to determine whether the antibodies are capable of fixing complement. Once colonies producing the desired antibodies have been identified, the colonies may be perpetuated to provide for a continued source of the desired antibodies.

To obtain hybridoma cell lines secreting monoclonal antibodies directed to a single antigenic determinant associated with lens epithelial cells, the hybridoma cells may be cloned using for example, limiting dilution. The stage at which the cells may be cloned is not critical to the invention, and may be before identification of colonies secreting antibodies of interest, or later. However, to avoid overgrowth of antibody-producing cells with non-antibody producing cells, the colonies are preferably cloned as soon after fusion as practicable.

For large scale production of antibodies, the hybridomas may introduced into the peritoneal cavity of a mammal and grown as an ascites tumor. Antibodies may then be isolated from the ascites fluid. Alternate methods for large scale production of monoclonal antibodies include inducing subcutaneous tumors using the method described above and collecting the blood from the animal. The hybridoma cells can also be grown on a large scale in tissue culture. Where the cells secrete the antibodies into the growth medium, the conditioned growth medium containing the antibodies can be collected for antibody isolation. Where the hybridoma cells do not secrete the antibodies, the cells may be collected, lysed using conventional means, and antibody purified from the cell lysate. Methods of purifying monoclonal antibodies are well known to those skilled in the art.

The complement is a standard complement. By complement is intended normal serum of man or other vertebrates which comprises about 9 major proteins which react with antigen-antibody complexes to cause damage to cell membranes, including lysis. Complement is usually supplied as serum, for example, rabbit serum. A typical complement and its preparation useful in the present invention is described in *Monoclonal Antibodies* (1980), Plenum Press New York, Eds. Kennett et al., pp. 391-392, which publication is incorporated herein by reference. Alternatively, it is possible to use patient complement activity which may be obtained in sufficient concentration from aqueous humor during surgery.

The preferred method for carrying out the subject invention will involve the instillation, immediately following cataract surgery, of about 25-200, preferably about 50-150, more preferably about 100 $\mu$l of monoclonal antibody capable of specifically binding to lens epithelial cells. Generally the monoclonal antibodies will be introduced in a physiologically acceptable solution, which may be saline, phospate-buffered saline, or the like and will have a concentration of about $10^8$-$10^{13}$, more usually about $10^9$-$10^{12}$ antibodies/ml. Alternatively, if performed at a time other than the initial cataract surgery, it will be necessary to either make an incision about the cornea for instillation of the monoclonal antibody, or to inject the antibody intracamerally into the anterior chamber.

After introduction of the monoclonal antibody and incubation for a sufficient time for the antibodies to bind to any remnant lens epithelial cells, usually about 30 minutes, the anterior chamber may be flushed to remove any unbound antibody. Complement (as, for example, an appropriate dilution of rabbit serum in a physiologically acceptable medium containing $Mg^{2+}$ and $Ca^{2+}$) is then introduced into the anterior chamber in an amount of from about 25-200, more usually from about 50-150 $\mu$l, which agent will be present in an amount sufficient to substantially completely or completely kill all of the lens epithelial cells. Generally, the cytolytic effect will be realized within a relatively short time after the introduction of complement, usually in about 0.5 hour, or shortly thereafter, when lysis of the target cells can be used to evaluate the onset of the cytolyic effect.

To prevent binding, either specific or nonspecific, to cells cross-reactive with the monoclonal antibody binding sites on the lens epithelial cells, prior to extracapsular extraction, an agent having cross-reactivity with the monoclonal antibody may be introduced into the anterior chamber. Typically this agent comprises Fab fragments prepared from the monoclonal antibody which can be used either alone or in conjunction with a non-specific protein such as human serum albumin, which may block non-specific binding sites. The monoclonal antibody and complement can then be introduced as described above.

The subject compositions can be provided as kits for use in one or more operations. The kits will usually include the monoclonal antibody and the complement which may be present as concentrates which may be further diluted prior to use or they may be provided at the concentration of use, where the vials may include one or more dosages. Conveniently, single dosages may be provided in syringes, contained in sterilized containers, so that the physician may employ the syringes directly, where the syringes will have the desired amount and concentration of agents. Thus, the kit may have a plurality of syringes containing the monoclonal antibodies as well as the complement in appropriate proportional amounts. Where the syringes contain the formulation for direct use, usually there will be no need for other reagents for use with the method.

The following examples are offered by way of illustration and not by way of limitation.

EXPERIMENTAL

Murine hybridoma cell line HBI-09302, which secretes an IgM antibody substantially specific for lens epithelial cells, was deposited with the American Type Culture Collection (ATCC), 12301 Parklawn Drive, Rockville, Md. 20852, U.S.A. on Mar. 5, 1987 and was given ATCC Accession No. HB 9343. Murine hybridoma cell line HBI-4197-X, which secretes an IgG$_3$ antibody substantially specific for lens epithelial cells, was deposited with the ATCC on Jun. 14, 1988 and was given ATCC Accession No. HB 9747.

EXAMPLE 1

Preparation of Monoclonal Antibodies

A. Immunization

Human lens epithelial cells were obtained as small sections of the anterior capsule during cataract surgery. They were collected aseptically and placed in RPMI1640 containing 10% fetal bovine serum (FBS). Viable cells could be maintained for at least two weeks. The human lens epithelial cells were emulsified in Freunds Complete Adjuvant. Mice (BALB/c) were immunized with lens epithelial cells; $5 \times 10^5$ cell equivalents per 200 $\mu$l were given per animal for the primary injection. Additional injections consisting of equivalent cell material emulsified in Freunds Incomplete Adjuvant were given intramuscularly 3 weeks apart. These mice received two additional injections of either ME180 cells or human amnion cells (WISH) prior to harvesting spleens for fusion.

B. Fusion

Spleens from immunized animals were removed three to five days following the last injection and prepared as a single cell suspension. The lymphocytes then were fused with P363/Ag8.653 mouse myeloma cells under conventional conditions. Following fusion, the cells were resuspended in Iscoves medium containing hypoxanthine, aminopterin, and thymidine (HAT medium) and placed in wells according to the number of myeloma cells to give a density of about $10^4$ cells/well. The cells were fed on days 5, 12, and 15 by removing and replacing half of the medium. Cultures identified as positive for antibody secretion by screening assays, were transfered to 24 well plates containing 1 ml Iscoves medium (IMDM) containing hypoxanthine and thymidine (HT), and were cloned three times by limiting dilution.

C. Screening (i) Binding to rabbit lens epithelial cells. Hybridoma supernatants were initially tested for binding using rabbit lens epithelial cells. Briefly, rabbit lens epithelial cells (RLE cells) were grown in 96-well dishes and fixed with 0.025% gluteraldehyde. Culture supernatants were added and incubated for one hour at 37° C. Bound antibody was detected using goat anti-mouse IgG horse radish peroxidase. Over 800 hybrids were analyzed. One hybridoma, 09302, was selected for use in this study. The antibody binds to both human and rabbit lens epithelial cells on freshly excised anterior capsule segments. In contrast it does not bind to lymphoid cells as determined by ELISA (see Table 1).

TABLE 1

| Reactivity of Mab 09302 with Tissue Culture Cell Lines by ELISA | |
|---|---|
| Cell Lines | Reactivity* |
| Rabbit lens epithelial | +++ |
| Human lymphocyte (Daudi) | − |

*ELISA absorbance value [O.D. 405 nm]

(ii) Specificity of Binding. Enucleated human eyes (Lions Eye Bank, Houston, Tex.) were frozen in liquid nitrogen and stored at −70° C. When needed, frozen tissue sections were prepared by cryostat and mounted on glass slides. Sections were stained with hybridoma culture supernatants containing monoclonal antibodies followed by goat anti-mouse antibody conjugated to horseradish peroxidase to detect bound mouse immunoglobulin. The substrate used was 3-amino-9-ethyl carbazole. Using this technique, supernatants from the hybridoma 9302 and 4197-X bound to lens epithelial cells. Other cellular structures in the eye front were not stained, namely corneal endothelial cells, iris epithelial cells, etc. Based upon the intensity of the staining, the relative intensity for lens epithelial cells was 4+, representing 100% of the lens epithelial cells were stained; less than 10% of other cell types within the anterior chamber were stained showing that the antibodies are substantially specific for lens epithelial cells.

(iii) Class Specificity of Monoclonal Antibody. Class and subclass of the murine hybridoma antibodies was determined using Ouchterlony analysis (see *Monoclonal Antibodies: Principles and Practice*, 2nd ed., Goding, Academic Press, New York, pg. 105, 1986, which publication is incorporated herein by reference). Using this technique it was determined that hybridoma 09302 produces an IgM antibody and that hybridoma 4197-X produces an IgG$_3$ antibody.

(iv) Complement Fixation. A sufficient number of target cells (rabbit lens epithelial cells (RLE)) were plated in 96-well culture plates to achieve 80–90% confluence. 09302 culture supernatant or control medium (100 $\mu$l/well) was added at various dilutions to the wells and incubated for 30 minutes at 37° C. Rabbit serum (Accurate Chemical and Scientific, Westbury, N.Y.) (5 $\mu$/well) was added and incubation continued for 12 hrs. Living cells were identified by their ability to convert the yellow dye 3-(4,5-dimethylthiazol-2-y-1)-2,5 diphenyl tetrazolium bromide (MTT) to a purple product. Cell viability was determined based upon the intensity of color development which was proportional to viability. Intensity of colored product was measured spectrophotometrically at an optical density (O.D.) of 570 nm (Mosmann, *J. Immunol.* (1983) 65:55).

TABLE 2

| Effect of 09302 Antibody and Complement on RLE Cells | | |
|---|---|---|
| 09302 Antibody Dilution of | Absorbance Reading at 570 nm | |
| Culture Supernatant | With Complement | Without Complement |
| 1 undiluted | 0.03 | 0.24 |
| 2 1:3 | <0.00 | 0.33 |
| 3 9 | <0.00 | 0.38 |

TABLE 2-continued

Effect of 09302 Antibody and Complement on RLE Cells

| 09302 Antibody Dilution of Culture Supernatant | | Absorbance Reading at 570 nm | |
|---|---|---|---|
| | | With Complement | Without Complement |
| 4 | 27 | <0.00 | 0.38 |
| 5 | 81 | 0.04 | 0.39 |
| 6 | 243 | 0.46 | 0.41 |
| 7 | | 0.48 | 0.41 |
| Control (No antibody) | | 0.49 | 0.48 |

As shown in Table 2, the addition of complement alone had no effect on cell viability, while the combination of antibody plus complement resulted in cell destruction.

(v) Indirect Staining. Rabbit lens epithelial cells were seeded onto sterile coverslips. The coverslips were washed with Hanks Balanced Salt Solution (HBSS) and fixed with 3% paraformaldehyde in HBSS 24 hours prior to assay. The coverslips were again washed with HBSS and then overlaid with hybridoma supernatants. After 1 hr of incubation at room temperature, the cover slips were washed again with HBSS and overlaid with diluted fluorescein isothiocyanate-labeled goat anti-mouse immunoglobulin. The coverslips were washed, then mounted on a microscope slide. Fluorescence microscopy was done with a Zeiss microscope. Photographs were taken using Kodak Tri-x film. Results indicate that 9302 binds to surface of RLE-cells.

EXAMPLE 2

Large Scale Antibody Production

Large scale production of a single monoclonal antibody was achieved by injecting about $10^7$ hybrid cells into appropriate H-2 compatible mice. The ascites tumors were induced by the following method. For ascites production, mice were injected intraperitoneally with 0.5 ml of pristane (2,6,10, 14-tetramethylpentadecane, Aldrich), and rested for 1-2 months. Three to four days prior to transfer of the interspecies hybridoma, each mouse was injected with 50 μl of antilymphocyte serum. On the day of tumor transfer, each mouse received total body irradiation (600-800 rads) followed 6-8 hours later by syngeneic bone marrow, $10^7$ cells mouse. Hybridoma cells ($10^6$-$10^7$) in Dulbeccos Modified Eagle's Medium were then injected intraperitoneally. As the tumors began to appear (10-30 days after injection), the mice were bled and the presence and concentrations of the antibodies in the serum continually tested. Appropriate antibodies were collected, purified and stored.

EXAMPLE 3

Prevention of Secondary Cataracts In Vivo

Long-term effectiveness of the subject treatment protocols are evaluated as follows. Antibodies and complement are injected into the anterior chambers of rabbits following extracapsular lens extraction. The long-term progress of the treated eyes is compared with that of the untreated eyes by ophthalmological observations and histological studies.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising:
   a hybridoma cell culture producing monoclonal antibodies which bind specifically to lens epithelial cells and have low or no cross reactivity with other cells found in the anterior segment of the eye and which activate complement.

2. A composition according to claim 1, wherein said lens epithelial cells are human.

3. A composition comprising:
   a monoclonal antibody which binds to an antigenic determinant on the surface of a lens epithelial cell and has low or no cross reactivity with other cells found in the anterior segment of the eye and which activates complement.

4. A composition according to claim 3, wherein said monoclonal antibody is classified as mouse IgM, IgG2a, IgG2b, or IgG3 antibody, or the equivalent thereof.

5. A composition comprising:
   a complement-fixing monoclonal antibody which binds specifically with lens epithelial cells and has low or no cross reactivity with other cells found in the anterior segment of the eye.

6. A composition according to claim 5, wherein said monoclonal antibody is produced by a hybridoma cell line having ATCC Accession No. HB 9343.

7. A hybridoma cell line having ATCC Accession No. HB 9343 or HB 9747.

8. A hybridoma produced by fusing spleen cells from a mouse immunized with an immunogen comprising epithelical cells with immortalized mouse B cells, wherein said cell line produces a monoclonal antibody which reacts with cell surface antigens of lens epithelial cells and acivates complement.

9. The hybridoma according to claim 8, wherein said antigens are not detectable on epithelial cells in the eye other than lens epithelial cells or is found on other epithelial cells in the eye having low or no cross reactivity with other cells found in the anterior segment as compared to said lens epithelial cells.

10. The hybridoma cell line according to claim 8, wherein immunoglobulin produced by said cell line is mouse immunoglobulin IgM or IgG3.

11. A monoclonal antibody produced by a cell line according to any one of claims 8, 9 and 10.

12. A murine hybridoma designated HBI-4197X, having ATCC Accession No. HB 9747.

13. A hybridoma which expresses monoclonal antibodies having the same antigenic specificity as that of monoclonal antibodies expressed by cell line HBI-4197X, ATCC Accession No. HB 9747.

14. Monoclonal antibodies derived from a hybridoma according to claim 12 or claim 13.

15. A monoclonal antibody fragment derived from a monoclonal antibody having the binding specificity of a monoclonal antibody according to claim 14.

16. Monoclonal antibodies according to claim 15, labelled with an agent capable of providing a detectable signal.

17. Monoclonal antibodies according to claim 13, labelled with an agent capable of providing a detectable signal.

* * * * *

UNITED STATES PATENT AND TRADEMARK OFFICE
CERTIFICATE OF CORRECTION

PATENT NO. : 5,202,252
DATED : April 13, 1993
INVENTOR(S) : Jared M. Emery, et. al.

It is certified that error appears in the above-indentified patent and that said Letters Patent is hereby corrected as shown below:

in column 6, line 51, "μ/well" should be --μl/well--;
in claim 8, col. 8, line 37, "epithelical" should be --epithelial--;
in claim 8, col. 8, line 39, "antigens" should be --antigen--;
in claim 8, col. 8, line 40, "acivates" should be --activates--;
in claim 9, col. 8, line 42, "antigens are" should be --antigen is--.

Signed and Sealed this

Nineteenth Day of July, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,202,252
DATED : April 13, 1993
INVENTOR(S) : Jared M. Emery; Dominic M.-K. Lam; Peter J. Kelleher It is certified that error appears in the above-indentified patent and that said Letters Patent is hereby corrected as shown below:

On the title page, item [73] Assignee, "Houston Biotechnology Incorporated, The Woodlands, Tex." should be --Baylor College of Medicine, Houston, Tex.--

Signed and Sealed this

Second Day of May, 1995

Attest:

BRUCE LEHMAN

Attesting Officer    Commissioner of Patents and Trademarks